United States Patent [19]

Kodama et al.

[11] Patent Number: 5,450,854
[45] Date of Patent: Sep. 19, 1995

[54] ALPHA-WAVE AMPLITUDE SELECTOR WITH WINDOW SLICER

[75] Inventors: Hiroyuki Kodama; Ichiro Hieda; Tomoyuki Yoshida, all of Higashi, Japan

[73] Assignee: Agency of Industrial Science and Technology, Tokyo, Japan

[21] Appl. No.: 156,637

[22] Filed: Nov. 24, 1993

[30] Foreign Application Priority Data

Nov. 24, 1992 [JP] Japan .................................. 4-336656

[51] Int. Cl.⁶ .......................................... A61B 5/0482
[52] U.S. Cl. ................................................ 128/732
[58] Field of Search ............................... 128/731–733

[56] References Cited

U.S. PATENT DOCUMENTS

| | | | |
|---|---|---|---|
| 3,882,850 | 5/1975 | Bailin et al. | 128/732 |
| 3,896,790 | 7/1975 | Dikmen | 128/732 |
| 4,013,068 | 3/1977 | Settle et al. | 128/732 |
| 4,334,545 | 6/1982 | Shiga | 128/732 |

Primary Examiner—Angela D. Sykes
Attorney, Agent, or Firm—Oblon, Spivak, McClelland, Maier, & Neustadt

[57] ABSTRACT

An alpha-wave amplitude selector with a window slicer quickly selects and detects a time domain in which the amplitude of alpha component in brain waves exceeds or falls below a given threshold levels for use in biofeedback. A combination of a window slicer that receives alpha wave as input and an RS flip-flop connected to the window slicer significantly reduces a time-delay between a point at which the amplitude of alpha wave exceeds or falls below a preset level and a point at which a feedback stimulus is given. The window slicer outputs a high pulse when the alpha wave exceeds a high threshold slice level and a window pulse when the alpha wave enters an intermediate region between the high and a low threshold slice level, remains below the high threshold slice level and falls below the low threshold slice level at the trailing edge, whereas the RS flip-flop outputs a high-alpha phase mark based on the high pulse and a low-alpha phase mark based on the window pulse and neglects any high pulses output between the generation of the above high pulse and that of the next window pulse.

6 Claims, 3 Drawing Sheets

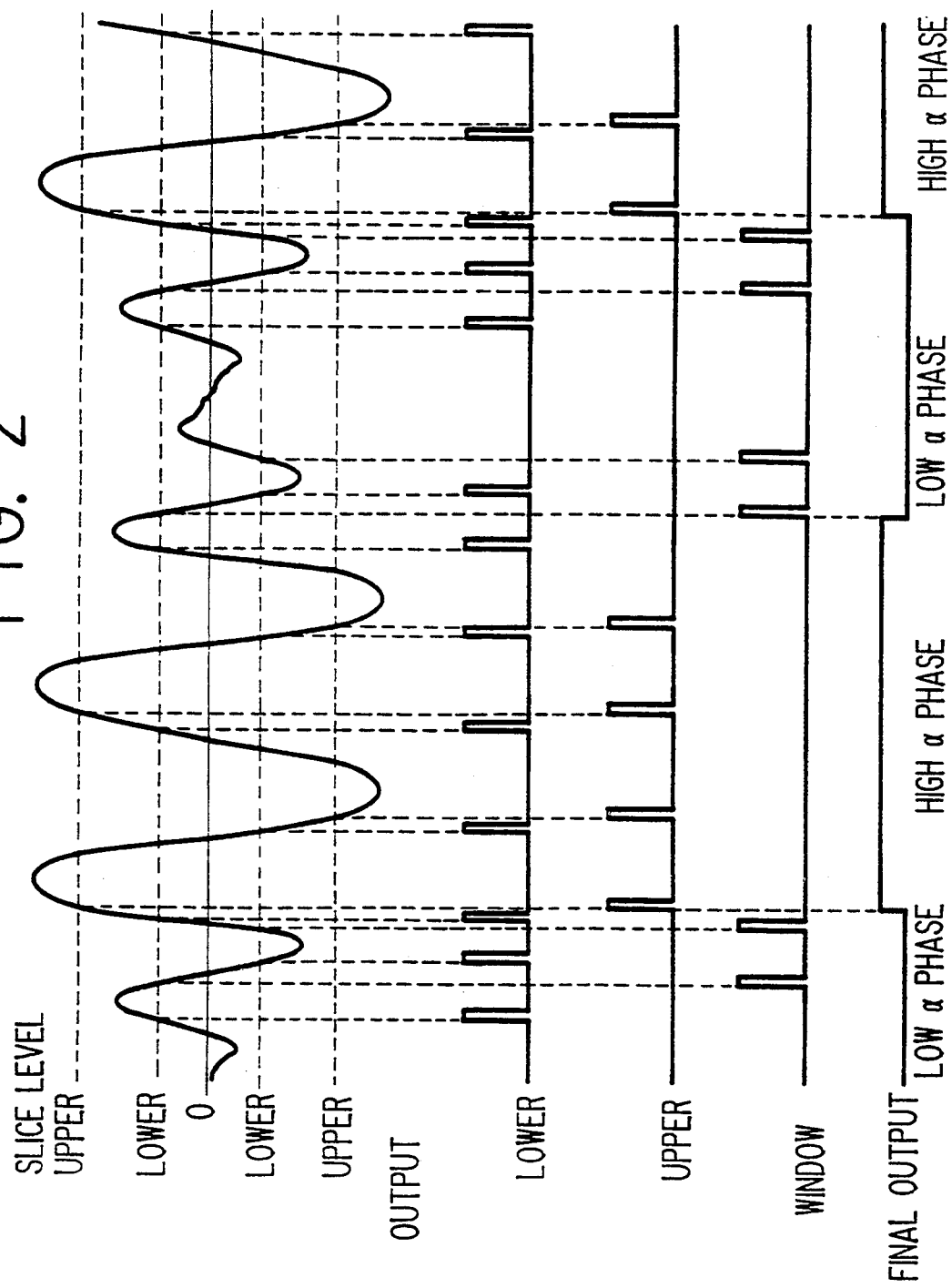

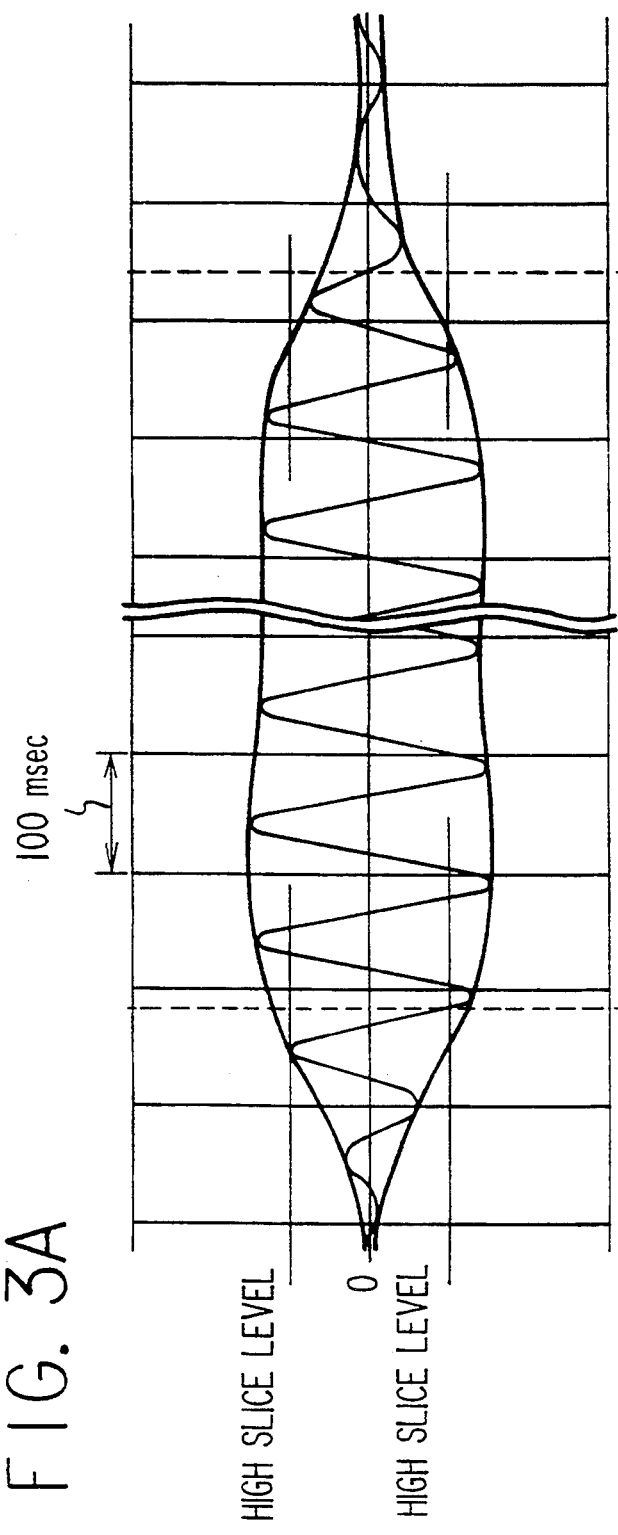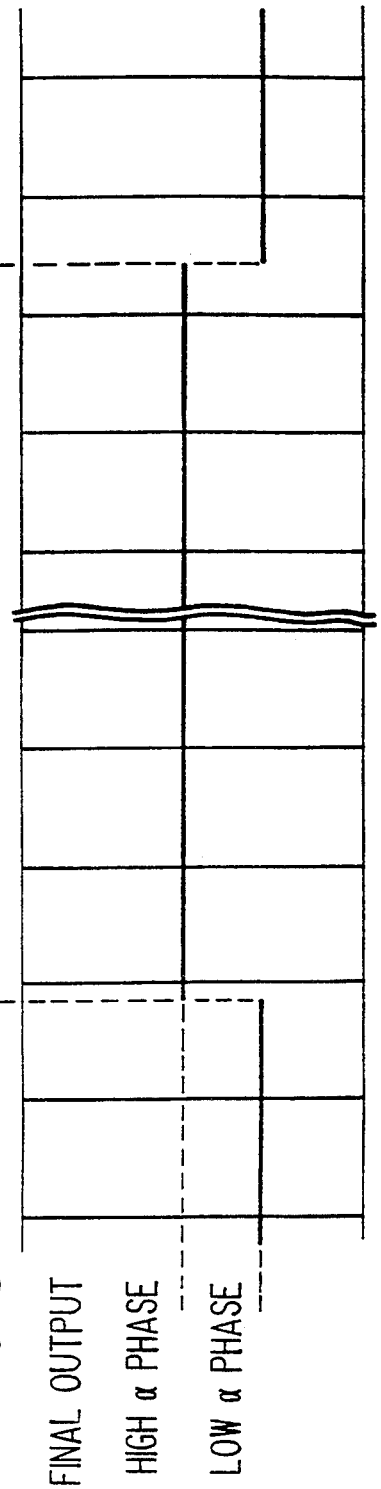

ALPHA-WAVE AMPLITUDE SELECTOR WITH WINDOW SLICER

FIELD OF THE INVENTION

This invention relates to an alpha-wave amplitude selector that quickly selects and detects a time domain in which the amplitude of an alpha-wave component of brain waves exceeds or falls below given levels for the purpose of biofeedback, and more particularly to an alpha-wave amplitude selector that quickly selects and detects such a time domain by the use of a window slicer and an RS flip-flop.

DESCRIPTION OF THE PRIOR ART

Biofeedback of alpha wave is used for the evaluation of perception characteristics of patients or subjects in medical treatment of alcohol dependence syndrome. In this application, the amplitude of alpha wave is converted into binary information representing a high-alpha phase whose amplitude is above a given level and a low-alpha phase whose amplitude is below another given level. The appearance pattern of each phase formed by the feedback of the information varies with various environmental stimuli, and the process of such variations is used for the evaluation of the diagnosis of subjects and the process of their treatment.

It has been known that the appearance pattern of the high- and low-alpha phases exhibits a higher degree of regularity with a shorter time-delay between a point at which the amplitude of alpha wave exceeds or falls below a preset level and a point at which a feedback stimulus is given. Therefore, means to minimize the time-delay are in constant demand.

In this type of evaluation, determination of the envelope of amplitude has been employed as a straightforward approach. This approach, however, suffers from substantial limitations in the real-time processing of amplitude information because it involves smoothing and other time-consuming steps.

This conventional method recognizes a time domain in which the envelope of the amplitude of alpha wave exceeds a given threshold level. For example, Boudrot developed a method that applies full-wave rectification to the alpha wave obtained by passing raw brain waves through a bandpass filter, inputs the obtained current into a modified direct-current meter, and smooths the current by using the mechanical inertia of the meter pointer (Boudrot, R.: Psychophysiology, 9. 461–466 (1972)). Mulholland et al. established a method to distinguish the high-alpha phase from the low-alpha phase by comparing the magnitude of the amplitude of alpha wave with a certain preset level and use the obtained data for biofeedback. Also, various studies concerning attention and other human functions have been made by examining the changes in the appearance pattern of the high- and low-alpha phases induced by the introduction of various environmental stimuli (Mulholland, T. and Eberlin, P.: Biofeedback and Self-Regulation, vol., No. 1, 43–57 (1977), and Mulholland, T., Goodman, D. and Boudrot, R.: Biofeedback and Self-Regulation, vol. 8, No. 4 585–600 (1983)).

Being a first-order lag element, the meter pointer excels in linearity. Usually, however, achievement of adequate smoothing requires as long a time as is approximately ten times the cycle of the object wave. In this respect, Mulholland et al. shortened the time-delay in smoothing through the improvement of the meter pointer.

Mulholland et al. also conducted a biofeedback test in which several steps of time-delay were set and each subject was informed of the appearance of his own alpha wave. In this test, the shortest time-delay of 0.25 second yielded the most stable alteration pattern of the high- and low-alpha phases (Mulholland, T., Boudrot, R. and Davidson, A.: Biofeedback and Self-Regulation, vol. 4, No. 2, 93–102 (1979)). This corresponds to the state in which the best feedback control of the alpha-wave component is achieved, as defined by Mulholland. Although further reduction of time-delay would bring about still better feedback control, no such improvement was realized by the aforementioned system.

SUMMARY OF THE INVENTION

The inventor came up with an idea that determination of the envelope is not necessarily an indispensable requirement because no other amplitude information is required as to the alpha-wave component of brain waves than the binary information above or below a given level, which, in turn, led to this invention through an attempt to substantially shorten the time-delay in the selection of the high-alpha phase.

Accordingly, an object of this invention is to provide a means for substantially shortening the time-delay between a point at which the amplitude of alpha wave exceeds or fails below the preset threshold level a point at which a feedback stimulus is given by directly distinguishing the high- and low-alpha phases without determining the envelope of the alpha wave.

Another object of this invention is to provide an alpha-wave amplitude selector that converts the amplitude of an alpha component of brain waves into binary information representing a high-alpha phase whose amplitude is above a given threshold level and a low-alpha phase whose amplitude is below another given threshold level by the use of a simple combination of a window slicer and an RS flip-flop.

In order to achieve the above objects, an alpha-wave amplitude selector according to this invention comprises a window slicer that receives alpha wave as an input, outputs a high pulse when the alpha wave exceeds a high threshold slice level and a window pulse when the alpha wave enters an intermediate region between the high and a low threshold slice level, remains below the high threshold slice level and falls below the low threshold slice level at the trailing edge and an RS flip-flop connected to the window slicer that outputs a high-alpha phase mark based on the high pulse and a low-alpha phase mark based on the window pulse and neglects any high pulses output between the generation of the above high pulse and that of the next window pulse.

This alpha-wave amplitude selector converts the amplitude of an alpha component of brain waves into binary information representing a high-alpha phase whose amplitude is above a given threshold level and a low-alpha phase whose amplitude is below another given threshold level by means of a simple combination of a window slicer and an RS flip-flop. Direct distinction between the high-and low-alpha phases without determining the envelope of the alpha wave permits quick selection of the desired alpha-wave amplitude.

Directly distinguishing the high-alpha phase from the low-alpha one without employing the conventional straightforward approach to determine the envelope of alpha wave, the alpha-wave amplitude selector according to this invention substantially reduces the time-delay between a point at which the amplitude of alpha wave exceeds or falls below the present threshold level and a point at which a feedback stimulus is given. This significant improvement offers a an important advantage tot he investigation of various information processing steps in human brains.

BRIEF DESCRIPTION OF THE DRAWINGS

FIG. 2 is a schematic waveform showing the relationship of alpha wave with the slice levels and output pulses of a window slicer and the final output of an alpha-wave amplitude selector.

FIG. 3 shows a simulated alpha wave at A and the high- and low-alpha phase marks obtained by inputting the simulated alpha wave into an alpha-wave amplitude selector at B.

DESCRIPTION OF THE PREFERRED EMBODIMENT

Figure 1:
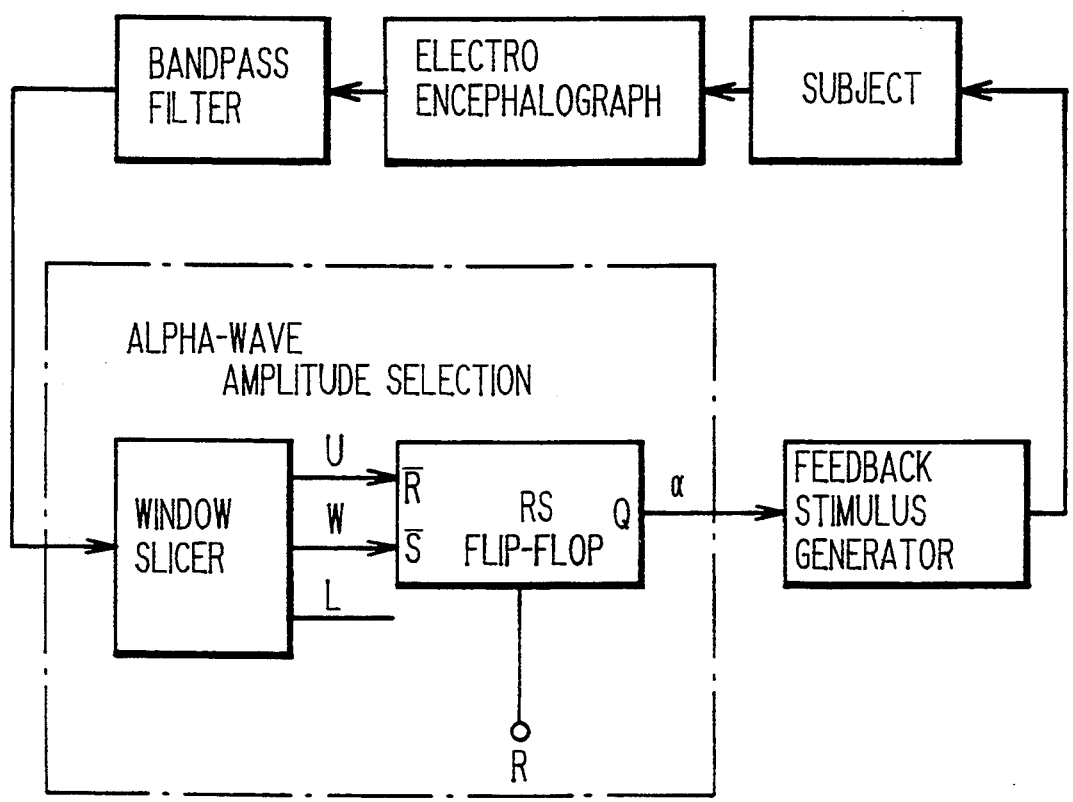
FIG. 1 is a block diagram showing the construction and function of an alpha-wave amplitude selector according to this invention.

FIG. 1 shows the construction and function of an alpha-wave amplitude selector according to this invention.

This alpha-wave amplitude selector essentially comprises a window slicer that receives alpha wave obtained by passing raw brain waves through a bandpass filter as an input and an RS flip-flop connected thereto. The alpha wave used as an input is obtained by passing brain waves collected by an electroencephalograph attached to the scalp of a subject through a bandpass filter that extracts only alpha wave.

A window slider used in an example described later is capable of setting two threshold slice levels, high and low, and performing bipolar processing using signals in all areas of he positive and negative domains. Concretely, the window slicer has three output pulses (low, high and window), as shown in FIG. 2. Output terminals L, U and W respectively emit a low pulse when the input signal of alpha wave falls below a low threshold slice level, a high pulse when the input signal exceeds a high threshold slice level, and a window pulse when the input signal enters an intermediate region between the low and high threshold slice levels, the input signal remains below the high threshold slice level and the input signal falls below the low threshold slice level at the trailing edge.

The RS flip-flop selects high- and low-alpha phases using the high and window pulses emitted by the window slicer. The RS flip-flop does not use the low pulse. The RS flip-flop has a high-pulse input terminal connected to the high-pulse output terminal $\overline{U}$ of the window slicer, a window-pulse input terminal connected to the window-pulse output terminal W, an output terminal $\alpha$ to emit a high-alpha phase mark and a reset terminal R to return the RS flip-flop to its initial condition. Here, the reset terminal R emits a low-alpha phase mark.

The RS flip-flop outputs a high-alpha phase mark from the output terminal $\alpha$ based on the high pulse that is emitted when alpha wave shifts from the low-alpha phase to the high-alpha phase and a low-alpha phase mark from the same terminal based on the window pulse that is emitted when alpha wave shifts from the high-alpha phase to the low alpha-phase. Any high pulses output between the high pulse and the window pulse described above are neglected.

The high- or low-alpha phase mark emitted as the final output is delivered to a feedback signal generator to present a feedback stimulus tot he subject, such as a stimulus to vary the level of brightness according to the high- or low-alpha phase.

Using a simple combination of the window slicer and RS flip-flop, the alpha-wave amplitude selector described above converts the amplitude of an alpha component of brain waves into binary information representing a high-alpha phase whose amplitude is above a given threshold level and a low-alpha phase whose amplitude is below another given threshold level. Direct distinction of the high-alpha phase from the low-alpha one without determining the envelope of the amplitude of alpha wave permits quick selection of the desired alpha-wave amplitude.

Care must be exercised in the setting of the low threshold slice level. A low threshold slice level set too close to a high threshold slice level could result in a failure to generate a window pulse. Then, a wrong output that the high-alpha phase continues uninterrupted could result even when observation of alpha wave clearly indicates the presence of both high- and low-alpha phases. On the other hand, a low threshold slice level too far away from a high threshold slice level could delay the selection of the start point of the low-alpha phase. When alpha wave decreases gradually, however, the maximum delay measured from a point at which the envelope of amplitude crossed the high threshold slice level is approximately three-fourth of the cycle of alpha wave. When alpha wave increases gradually, the delay in the selection of the start point of the high-alpha phase measured from the same point is not more than half of the cycle.

The result of a simulation test conducted by using an alpha-wave amplitude selector according to this invention is described below.

The simulation test was made on a simulated alpha wave obtained by inputting frequencies obtained from a sine wave of 10 Hz passed through a rectangular gate into a bandpass filter (with a frequency range of 8 to 13 Hz and a damping property of 48 dB/oct.).

FIG. 3 shows the simulated alpha wave at A and the high- and low-alpha phase marks obtained by inputting the simulated alpha wave in the alpha-wave amplitude selector at B. The low threshold slice level employed in this simulation test was at 0.

As can be seen from a comparison between A and B of FIG. 3, the leading edge at A substantially agrees with a point at which the waveform of the simulated alpha wave exceeds the high threshold slice level (in the negative domain). This means that a feedback stimulus is presented with practically no time-delay. A comparison of the envelope of the amplitude of the simulated alpha wave with the high- and low-alpha phase marks at B reveals a time-delay of approximately 0.03 second at the leading edge and approximately 0.05 second at the trailing edge. These time-delays correspond to approximately a quarter and a half of the cycle of the simulated alpha wave, respectively.

Another test was also conducted on a subject who sat in front of a hemispherical vision-field equalizer that makes the brightness of the entire field of the subject's vision uniform. Brain waves were taken through bipolar electrodes attached to the left and right occipital and parietal regions. The brain waves taken from the left regions were led to the alpha-wave amplitude selector through a bandpass filter (8 to 13 Hz). The output from the alpha-wave amplitude selector input into the vision-field equalizer actuated the illuminating unit therein to make the field of vision brighter in the high-alpha phase than in the low-alpha phase. The feedback loop thus formed enabled the subject to learn the condition of his own alpha wave.

Before starting the feedback test, the appearance of alpha wave from the subject lying quietly with closed eyes was observed to determine the amplitude of bursting alpha wave. During the feedback test, the subject opened his eyes to permit the observation of his response to the photic feedback stimuli.

The high threshold slice level in the test was set at 25%, 35% and 45% of the amplitude of the burst alpha wave observed with the subject lying quietly with closed eyes. While the alpha phase appeared in a uniform stable pattern at 45%, more varied or disturbed patterns resulted from 25% and 35%.

What is claimed is:

1. An alpha-wave amplitude slicer comprises:
    a window slicer that receives an alpha wave as an input, outputs a first high pulse when the alpha wave exceeds a high threshold slice level and a window pulse when the alpha wave enters an intermediate region between the high and a low threshold slice level, the alpha wave remains below the high threshold slice level and the alpha wave falls below the low threshold slice level at a trailing edge; and
    an RS flip-flop connected to the window slicer that outputs a high-alpha phase mark based on the first high pulse and a low-alpha phase mark based on the window pulse and neglects any second high pulse output between the generation of the above first high pulse and that of the next window pulse.

2. An alpha-wave amplitude slicer according to claim 1, further comprising: a bandpass filter extracting only the alpha wave for input from brain waves detected by an electroencephalograph attached to a subject connected to said bandpass filter and an output from the bandpass filter is input into the window slicer.

3. An alpha-wave amplitude slicer according to claim 1, in which the window slicer, includes a function of bipolar processing by setting a low and a high threshold slice level and using signals in all areas of positive and negative domains.

4. An alpha-wave amplitude slicer according to claim 3, in which the window slicer has terminals to output a low, a high and a window pulse, with each terminal outputting the low pulse when the input alpha wave falls below the low threshold slice level, outputting the high pulse when the input alpha wave exceeds the high threshold slice level, and outputting the window pulse when the input alpha wave enters an intermediate region between the high and low threshold slice levels, remains below the high threshold slice level and falls below the low threshold slice level at the trailing edge.

5. An alpha-wave amplitude slicer according to claim 4, in which the RS flip-flop further comprises:
    a high-pulse input terminal connected to the high-pulse output terminal of the window slicer;
    a window-pulse input terminal connected to a window-pulse output terminal of the window slicer;
    an output terminal to emit a high-alpha phase mark; and
    a reset terminal to return the RS flip-flop to its initial condition, the reset terminal being adapted to emit a low-alpha phase mark as the initial condition.

6. An alpha-wave amplitude slicer according to claim 1, wherein a final output of high- or low-alpha phase mark is sent to a feedback signal generator that gives a feedback stimulus to the subject.

* * * * *

UNITED STATES PATENT AND TRADEMARK OFFICE
CERTIFICATE OF CORRECTION

PATENT NO. : 5,450,854

DATED : September 19, 1995

INVENTOR(S) : Hiroyuki KODAMA, Ichiro HIEDA, Tomoyuki YOSHIDA

It is certified that error appears in the above-indentified patent and that said Letters Patent is hereby corrected as shown below:

Column 1, line 9, after "below" insert --a--;
    line 9, change "levels" to --level--;
    lines 22-23, change "another given" to --the same--.

Column 2, line 29, change "fails" to --falls--;
    line 38, change "another given" to --the same--;
    lines 60-61, change "another given" to --the same--.

Column 3, line 43, change "falls below" to --exceeds--.

Column 4, line 14, change "another given" to --the same--.

Column 6, line 16, change "falls below" to --exceeds--.

Abstract, line 4, delete "or falls below";
    line 9, delete "or falls below";
    line 15, change "falls below" to --exceeds--;
    line 16, change ", whereas the" to --.  The--.

Signed and Sealed this

Twenty-seventh Day of February, 1996

Attest:

BRUCE LEHMAN

Attesting Officer      Commissioner of Patents and Trademarks